United States Patent
Suazon et al.

(10) Patent No.: US 6,613,732 B2
(45) Date of Patent: Sep. 2, 2003

(54) MULTILAYER CLEANING WIPE

(75) Inventors: Lamberta Suazon, Ajax (CA); Dawne Barry, Stouffville (CA); John Fletcher, Oakville (CA); Karen Wisniewski, Bound Brook, NJ (US); Barbara Thomas, Princeton, NJ (US); Albert R. Kelly, Douglaston, NY (US); Gerard Scheubel, Quebec (CA)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/107,901

(22) Filed: Mar. 27, 2002

(65) Prior Publication Data

US 2003/0104966 A1 Jun. 5, 2003

Related U.S. Application Data

(63) Continuation-in-part of application No. 10/008,715, filed on Nov. 13, 2001, now Pat. No. 6,440,925.

(51) Int. Cl.[7] .............................................. C11D 17/00
(52) U.S. Cl. ................... 510/438; 510/295; 510/499; 510/501; 510/503; 510/505; 510/506; 510/470; 134/42; 428/288; 15/209.1
(58) Field of Search ...................... 510/438, 295, 510/499, 501, 503, 505, 506, 470; 134/42; 428/288; 15/209.1

(56) References Cited

U.S. PATENT DOCUMENTS

| | | | | |
|---|---|---|---|---|
| 5,141,803 A | * | 8/1992 | Pregozen | 428/288 |
| 6,284,259 B1 | * | 9/2001 | Beerse et al. | 424/404 |
| 6,340,663 B1 | * | 1/2002 | Deleo et al. | 510/438 |
| 6,432,904 B1 | * | 8/2002 | Suazon et al. | 510/438 |

* cited by examiner

*Primary Examiner*—Necholus Ogden
(74) *Attorney, Agent, or Firm*—Richard E. Nanfeldt

(57) ABSTRACT

A cleaning wipe comprising a multi layer needlepunched fabric wherein the fabric is impregnated with a cleaning composition.

12 Claims, No Drawings

MULTILAYER CLEANING WIPE

RELATED APPLICATION

This application is a continuation in part application of U.S. Ser. No. 10/008,715 filed Nov. 13, 2001. Now U.S. Pat. No. 6,440,925.

FIELD OF INVENTION

The present invention relates to a cleaning wipe which is multi layer fabric substrate has been impregnated with a liquid cleaning composition.

BACKGROUND OF THE INVENTION

The patent literature describes numerous wipes for both body cleaning and cleaning of hard surfaces but none describe wipes for cleaning dishware, flatware, pots and pans. U.S. Pat. Nos. 5,980,931, 6,063,397 and 6,074,655 teach a substantially dry disposable personal cleansing product useful for both cleansing and conditioning the skin and hair. U.S. Pat. No. 6,060,149 teaches a disposable wiping article having a substrate comprising multiple layers.

U.S. Pat. Nos. 5,756,612; 5,763,332; 5,908,707; 5,914,177; 5,980,922 and 6,168,852 teach cleaning compositions which are inverse emulsions.

U.S. Pat. Nos. 6,183,315 and 6,183,763 teach cleaning compositions containing a proton donating agent and having an acidic pH. U.S. Pat. Nos. 5,863,663; 5,952,043; 6,063,746 and 6,121,165 teaches cleaning compositions which are oil in water emulsions.

SUMMARY OF THE INVENTION

A single use cleaning wipe for dishwashing application comprises a water insoluble substrate comprising a top flame treated polypropylene needlepunched layer having an abrasive surface, a center absorbent cellulose core layer and a bottom fine fiber polyester layer, wherein the top layer, center layer and bottom layer are needlepunched together, impregnated with a cleaning composition containing an anionic sulfonated surfactant, an alkyl polyglucoside surfactant, an alkyl monoalkanol amide, an ethoxylated alkyl ether sulfate surfactant, a $C_1$–$C_4$ alkanol and water.

The liquid cleaning compositions of this invention are not an emulsion and do not contain proteins, enzymes, sodium hypochlorite, dimethicone, N-methyl-2-pyrrolidone, monoalkyl phosphate or silicone based sulfosuccinate.

DETAILED DESCRIPTION OF THE INVENTION

The present invention relates to a cleaning wipe for dishware, flatware, pots and pans which comprises approximately:

(a) 20 wt. % to 95 wt. % of a water insoluble substrate comprising a top flame treated polypropylene needlepunched layer having an abrasive surface, a center absorbent cellulose core layer and a bottom fine fiber polyester layer, wherein the top layer, center layer and bottom layer are needlepunched together; and (b) 5 wt. % to 80 wt. % of a liquid cleaning composition being impregnated in said water insoluble substrate, wherein said liquid cleaning composition comprises:
  (i) 20 wt. % to 30 wt. % of an alkaline earth or alkali metal salt of an anionic sulfonated surfactant;
  (ii) 2 wt. % to 12 wt. % of an alkali metal salt of an ethoxylated alkyl ether sulfate surfactant;
  (iii) 0.5 wt. % to 10 wt. % of an alkyl polyglucoside surfactant;
  (iv) 0.5 wt. % to 6 wt. % of a $C_{12}$–$C_{14}$ alkyl monoalkanol amide such as lauryl monalkanol amide;
  (v) 1 wt. % to 8 wt. % of a $C_1$–$C_4$ alkanol;
  (vi) 0 to 5 wt. %, more preferably 0.1 wt. % to 4 wt. % of a proton donating agent;
  (vii) 0 to 6 wt. %, more preferably 0.1 wt. % to 4 wt. % of a polyethylene glycol;
  (viii) 0 to 6 wt. %, more preferably 0.5 wt. % to 5 wt. % of sodium xylene sulfonate and/or sodium cumene sulfonate; and
  (ix) the balance being water.

The present invention also relates to a cleaning wipe which comprises approximately:

(a) 20 wt. % to 95 wt. % of a water insoluble substrate comprising a top flame treated polypropylene needlepunched layer having an abrasive surface, a center absorbent cellulose core layer and a bottom fine fiber polyester layer, wherein the top layer, center layer and bottom layer are needlepunched together;

(b) 5 wt. % to 80 wt. % of a liquid cleaning composition being impregnated in said water insoluble substrate, wherein said liquid cleaning composition comprises:
  (i) 2 wt. % to 12 wt. % of an alkaline earth metal salt of a sulfonate surfactant;
  (ii) 2 wt. % to 12 wt. % of an alkali metal salt of a sulfonate surfactant;
  (iii) 5 wt. % to 18 wt. % of an alkali metal salt of an ethoxylated alkyl ether sulfate surfactant;
  (iv) 5 wt. % to 18 wt. % of an alkyl polyglucoside surfactant;
  (v) 1 wt. % to 10 wt. % of an amine oxide surfactant;
  (vi) 1 wt. % to 8 wt. % of a $C_1$–$C_4$ alkanol;
  (vii) 0.5 wt. % to 6 wt. % of sodium xylene sulfonate and/or sodium cumene sulfonate; and
  (viii) the balance being water.

Suitable water-soluble non-soap, anionic surfactants used in the instant compositions include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an α-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the $C_8$–$C_{18}$ alkyl sulfate salts the ethoxylated $C_8$–$C_{18}$ alkyl ether sulfate salts having the formula $R(OC_2H_4)n\ OSO_3M$ wherein n is 1 to 12, preferably 1and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)nOX\ COOH$ wherein n is a number from 4 to 12, preferably 5 to 10 and X is selected from the group consisting of

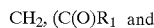

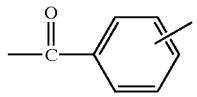

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

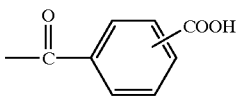

and $C_{10}$–$C_{12}$ alkyl ether polyethenoxy (5–7) CH2COOH. These compounds may be prepared by condensing ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

The amine oxide semi-polar nonionic surfactants comprise compounds and mixtures of compounds having the formula

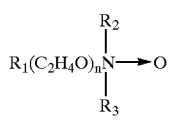

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

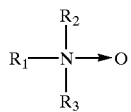

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 which is hereby incorporated herein by reference.

The alkyl polysaccharides surfactants, which are used in conjunction with the anionic surfactants have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4- positions rather than at the 1-position, (thus giving e.g. a glucosyl or galactosyl as opposed to a glucoside or galactoside). However, attachment through the 1- position, i.e., glucosides, galactoside, fructosides, etc., is preferred. In the preferred product the additional saccharide units are predominately attached to the previous saccharide unit's 2-position. Attachment through the 3-, 4-, and 6- positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula

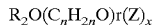

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, PA. APG25 is a nonionic alkyl polyglycoside characterized by the formula:

wherein n=10 (2%); n=122 (65%); n=14 (21–28%); n=16 (4–8%) and n=18 (0.5%) and x (degree of polymerization) =1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35C, 21 spindle, 5–10 RPM of 3,000 to 7,000 cps.

The anionic and alkyl polyglucoside surfactants discussed above are solubilized in an aqueous medium comprising water and optionally, solubilizing ingredients such as $C_1$–$C_4$ alkanols and dihydroxy alkanols such as ethanol isopropanol and propylene glycol. Suitable water soluble hydrotropic salts include sodium, potassium, ammonium and mono-, di- and triethanolammonium salts of xylene and cumene sulfonates. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10 ° C. Therefore, the proportion of solubilizer generally will be from about 1 % to 15%, preferably 2% to 12%, most preferably 3% to 8%, by weight of the detergent composition with the proportion of ethanol, when present, being 5% of weight or less in order to provide a composition having a flash point above about 46° C. Preferably the solubilizing ingredient will be a mixture of ethanol and either sodium xylene sulfonate or sodium cumene sulfonate or a mixture of said sulfonates or ethanol and urea. Inorganic salts such as sodium sulfate, magnesium sulfate, sodium chloride and sodium citrate can be added at concentrations of 0.5 to 4.0 wt. % to modify the cloud point of the nonionic surfactant and thereby control the haze of the resultant solution. Various other ingredients such as urea at a concentration of about 0.5 to 4.0 wt. % or urea at the same concentration in combination with ethanol at a concentration of about 0.5 to 4.0 wt. % can be used as solubilizing agents. Other ingredients which have been added to the compositions at concnetrations of about 0.1 to 4.0 wt. percent are perfumes, sodium bisulfite, ETDA, isoethanoeic and proteins such as lexine protein.

Polyethylene glycol maybe is used in the instant composition has a molecular weight of 200 to 1,000 wherein the polyethylene glycol has the structure

wherein n is 4 to 52. The concentration of the polyethylene glycol in the instant composition is 0 to 7 wt. %, more preferably 0.1 wt. % to 5 wt. %.

The proton donating agent is selected from the group consisting of inorganic acids such as sulfuric acid and hydrochloric acid and hydroxy containing organic acid, preferably a hydroxy aliphatic acid, which are selected from the group consisting of lactic acid or citric acid, orthohydroxy benzoic acid or citric acid or glycolic and mixtures thereof.

The water is present in the composition at a concentration of about 5 wt. % to 70 wt. %.

The cleaning composition of this invention may, if desired, also contain other components either to provide additional effect or to make the product more attractive to the consumer. The following are mentioned by way of example: Antibacterial agents such as 2,4,4'-trichloro-2'hydroxydiphenyl ether colors or dyes in amounts up to 0.5% by weight; preservatives or antioxidizing agents, such as formalin, 5-bromo-5-nitro-dioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed.

The product of the present invention comprises a water insoluable substrate with one or more layers. Each layer may have different textures and abrasiveness. Differing textures can result from the use of different combinations of materials or from the use of different manufacturing processes or a combination thereof. A dual texture substrate can be made to provide the advantage of a more abrasive side for cleaning difficult to remove soils. A softer side can be used for fine dishware and flatware. The substrate should not dissolve or break apart in water. It is the vehicle for delivering the cleaning composition to dishware, flatware, pots and pans. Use of the substrate enhances lathering, cleaning and grease removal.

A wide variety of materials can be used as the substrate. It should have sufficient wet strength, abrasivity, loft and porosity. Examples include, non woven substrates, wovens substrates, hydroentangled substrates and sponges.

Examples of suitable non woven water insoluable substrates include, 100% cellulose Wadding Grade 1804 from Little Rapids Corporation, 100% polypropylene needlepunch material NB 701-2.8 —W/R from American Nonwovens Corporation, a blend of cellulosic and synthetic fibres-Hydraspun 8579 from Ahistrom Fibre Composites, and 70% Viscose/30% PES Code 9881 from PGI Nonwovens Polymer Corp.

Another composite material manufactured by Texcel from a layer of coarse fiber 100% polypropylene needlepunch, an absorbent cellulose core and a fine fiber polyester layer needlepunched together. The polypropylene layer can range from 1.5 to 3.5 ox/sq. yd. The cellulose core is a creped paper layer ranging from 0.5 to 2 ox/sq. yd. The fine fiber polyester layer can range from 0.5 to 2 oz/sq. yd.

Still another composite material manufactured by Texcel from a layer of coarse fiber 100% polypropylene needlepunch, an absorbent cellulose core and a fine fiber polyester layer needlepunched together. The polypropylene layer can range from 1.5 to 3.5 oz/sq. yd. The cellulose core is a creped paper layer ranging from 0.5 to 2 oz/sq. yd. The fine fiber polyester layer can range from 0.5 to 2 oz/sq. yd. The polypropylene layer is flame treated to further increase the level of abrasivity. The temperature of the flame and the length of time the material is exposed can be varied to create different levels of surface roughness.

The abrasiveness is tested by cutting one quarter inch thick Lucite boards to fit an abrader bed. The boards are marked to indicate the track of the wipes during abrasion (approximately 2 ¼ and 4 ½ inches from one long edge) and three spots along the track (6, 9 and 12 inches from the short end). This gives unique and reproducible locations at which to do gloss measurements which are in the center of the abrasion track.

Using a BYK-Gardener Haze-Gloss glossmeter, the indicated spots are measured for starting gloss. An average and standard deviation is reported for each track using the three measurements.

Pieces of the wipes are cut approximately 3 inches by 2 inches. This piece is wrapped around a piece of sponge that fits in a holder for the abrader. (Indication should be made of whether the material is being used in the machine or cross direction). This wrapped sponge is placed in the holder, tucking all the edges of the wipe into the holder so that it is kept firmly in place. The dry sponge is wetted with approximately 20–25 g of water (either deionized, distilled or tap as the experiment desires). This is done so that there are two wipes in the trial.

The gloss measured Lucite board is placed in the abrader bed. Set the abrader for 500 cycles and start.

After the abrader cycles have ended, the Lucite board is removed. It is wiped dry with paper towel to remove any residual water. It is also inspected for any fingerprints incurred during handling and these are also wiped clean. Remeasure the gloss at the specified spots again and again report the average of these three spots and the standard deviation for each track.

The higher the abrasiveness of the wipe, the more that it roughens the surface of the Lucite and the more the gloss is reduced. The most abrasive of the wipes therefore give the greatest decrease in gloss. Results for this test are given below.

| Material (all machine direction) | Change in Gloss for 500 cycles |
|---|---|
| 3 layer needlepunch (Texel) no flame treatment | 0 |
| 3 layer needlepunch (Texel) medium flame treatment | 4 |
| 3 layer needlepunch (Texel) high flame treatment | 19 |

Ahistrom Manufacturers:

A hydroentangled nonwoven created from a blend of cellulosic and polyester and/or polypropylene fibers with an abrasive side. The basis weight can range from 1.2 to 6 ounces per square yard.

Kimberly Clark Manufacturers:

A composite dual textured material manufactured by Kimberly Clark comprises a coarse meltblown polypropylene, polyethylene, or polyester and high loft spunbond polyester. The two materials can be laminated together using chemical adhesives or by coprocessing the two layers. The coarse meltblown layer can range from 1 to 3 ounces per square yard while the highloft spunbond layer can range from 1 to 3 ounces per square yard.

Another example of a composite is a dual textured material composed of coarse meltblown polypropylene, polyethylene, or polyester and polyester/cellulose coform. The two materials can be laminated together using chemical adhesives or by coprocessing the two layers. The coarse meltblown layer can range from 1 to 3 ounces per square yard. The coform layer can range in composition from 30% cellulose and 70% polyester to 70% cellulose and 30% polyester and the basis weight can range from 1.5 to 4.5 ounces per square yard.

The product of the present invention comprising mutliple layers may be ultrasonically bonded after applying the coating of one or more of the layers. Alternatively layers may be bonded together by needlepunch, thermal bonding, chemical bonding, or sonic bonding prior to applying the coating.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following compositions (in wt. %) were prepared by simple batch mixing at room temperature. The cleaning wipe was made by the previously described impregnation process.

|  | A | B |
|---|---|---|
| Part I |  |  |
| Ammonium ethoxylated alkyl ether sulfate | 15.34 |  |
| Magnesium linear alkyl benzene sulfonate | 26.6 |  |
| Lauryl polyglucoside | 3.3 |  |
| Lauramide myristamide monoethanol amide | 3.5 |  |
| Sodium xylene sulfonate | 4.0 |  |
| Ethanol | 1.8 |  |
| Sodium bisulfite | 0.2 |  |
| HEDTA | 0.67 |  |
| Preservative | 0.47 |  |
| Water | Bal. |  |
| Part 1 Formula A | 1 | 3 |
| NB-701-2.8/WR fabric | 1 |  |
| Wadding Grade 1804 |  | 1 |
| SRF #8265C |  | 1 |
| SRF 1262 |  | 1 |

While particular embodiments of the invention and the best mode contemplated by the inventors for carrying out the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

EXAMPLE 2

The following formula was prepared at room temperature by simple liquid mixing procedures as previously described. The liquid formulation was then applied to the nonwoven substrate at room temperature.

|  | A |
|---|---|
| Part I Formulation |  |
| Water | Balance |
| Magnesium LAS | 9.00 |
| NaLAS | 3.00 |
| NH4 AEOS 1.3 EO | 11.5 |
| APG 625 | 10.0 |
| Lauryl myristyl amidopropyl amine oxide | 5.34 |
| Perfume | 0.45 |
| Color solution | 0.18 |
| pH | 6.75 |
| Part II Composite |  |
| Formulation A | 49.0 |
| 3 layer needlepunch[1] flame treated | 51.0 |

[1]Top layer flame treated 100% polypropylene (47%), center cellulosic wadding layer (26.5%) and bottom fine fabric polyester layer (26.5%) (Three layers needlepunched together).

What is claimed:

1. A hard surface cleaning wipe which comprises approximately:
    (a) 20 wt. % to 95 wt. % of a water insoluble substrate comprising a top flame treated polypropylene needlepunched layer having an abrasive surface, a center absorbent cellulose core layer and a bottom fine fiber polyester layer, wherein the top layer, center layer and bottom layer are needlepunched together; and
    (b) 5 wt. % to 80 wt. % of a liquid cleaning composition being impregnated in said water insoluble substrate, wherein said liquid cleaning composition comprises:
        (i) 20 wt. % to 30 wt. % of an anionic sulfonate surfactant;
        (ii) 2 wt. % to 12 wt. % of an anionic sulfate surfactant;
        (iii) 0.5% to 10% of an alkyl polyglucoside surfactant;
        (iv) 0.5 wt. % to 6 wt. % of a $C_{12}$–$C_{14}$ alkyl monoalkanol amide such as lauryl monalkanol amide;
        (v) 1 wt. % to 8 wt. % of a $C_1$–$C_4$ alkanol;
        (vi) about 2% by weight of a preservative selected from the group consisting of 5-bromo-5-nitro-dioxan-1,3 and 5-chloro-2-methyl-4-isothaliazolin-3-one; and
        (vii) the balance being water.

2. The wipe according to claim 1, further including an alkali metal salt of cumene sulfonate or xylene sulfonate.

3. The wipe according to claim 1, wherein said sulfonate surfactant is a linear $C_{10}$–$C_{16}$ alkyl benzene sulfonate.

4. The wipe according to claim 1, wherein said sulfate surfactant is an ethoxylated $C_8$–$C_{18}$ alkyl ether sulfate.

5. The wipe according to claim 1, further including about 0.01 to about 1.5 wt. % of a perfume.

6. The wipe according to claim 1, further including a proton donating agent.

7. The wipe according to claim 1, further including a polyethylene glycol.

8. The wipe according to claim 6, further including a polyethylene glycol.

9. The wipe according to claim 1, wherein said water insoluble substrate comprises one or more materials selected from nonwoven substrates, woven substrates, hydroentangeld substrates and sponges.

10. A method of manufacturing a product according to claim 1, wherein the cleaning composition is added or impregnated into the water insoluble substrate by spraying, dipping, extrusion coating or slot coating.

11. The wipe according to claim 1, wherein said liquid cleaning composition includes sodium xylene sulfonate and/or sodium cumene sulfonate.

12. A cleaning wipe which comprises approximately:
    (a) 20 wt. % to 95 wt. % of a water insoluble substrate comprising a top flame treated polypropylene needlepunched layer having an abrasive surface, a center absorbent cellulose core layer and a bottom fine fiber polyester layer, wherein the top layer, center layer and bottom layer are needlepunched together;
    (b) 5 wt. % to 80 wt. % of a liquid cleaning composition being impregnated in said water insoluble substrate, wherein said liquid cleaning composition comprises:
        (i) 2 wt. % to 12 wt. % of an alkaline earth metal salt of a sulfonate surfactant;
        (ii) 2 wt. % to 12 wt. % of an alkali metal salt of a sulfonate surfactant;
        (iii) 5 wt. % to 18 wt. % of an alkali metal salt of an ethoxylated alkyl ether sulfate surfactant;
        (iv) 5 wt. % to 18 wt. % of an alkyl polyglucoside surfactant;
        (v) 1 wt. % to 10 wt. % of an amine oxide surfactant;
        (vi) I wt. % to 8 wt. % of a $C_1$–$C_4$ alkanol;
        (vii) 0.5 wt. % to 6 wt. % of sodium xylene sulfonate and/or sodium cumene sulfonate; about 2% by weight of a preservative selected from the group consisting of 5-bromo-5-nitro-dioxan-1,3 and 5-chloro-2-methyl-4-isothaliazolin-3-one; and
        (viii) the balance being water.

* * * * *